(12) United States Patent
Walterspiel

(10) Patent No.: US 11,774,030 B2
(45) Date of Patent: Oct. 3, 2023

(54) TUBING CONNECTOR FOR DECREASED CONTAMINATION

(71) Applicant: Juan Nepomuc Walterspiel, Menlo Park, CA (US)

(72) Inventor: Juan Nepomuc Walterspiel, Menlo Park, CA (US)

(*) Notice: Subject to any disclaimer, the term of this patent is extended or adjusted under 35 U.S.C. 154(b) by 0 days.

(21) Appl. No.: 18/171,529

(22) Filed: Feb. 20, 2023

(65) Prior Publication Data

US 2023/0204148 A1 Jun. 29, 2023

Related U.S. Application Data

(63) Continuation of application No. 17/018,462, filed on Sep. 11, 2020, which is a continuation-in-part of application No. 15/789,388, filed on Oct. 20, 2017, now abandoned, which is a continuation of application No. PCT/US2016/047058, filed on Aug. 15, 2016.

(60) Provisional application No. 62/180,201, filed on Jun. 16, 2015.

(51) Int. Cl.
*F16L 35/00* (2006.01)
*F16L 58/18* (2006.01)
*A61M 39/16* (2006.01)

(52) U.S. Cl.
CPC ......... *F16L 58/185* (2013.01); *A61M 39/165* (2013.01)

(58) Field of Classification Search
CPC ......... F16L 58/18; F16L 58/185; F16L 35/00; F16L 35/005; F16L 2201/20; F16L 2201/40; F16L 2201/44; A61M 39/165; A61M 39/20; A61M 2039/1066
See application file for complete search history.

(56) References Cited

U.S. PATENT DOCUMENTS

| | | |
|---|---|---|
| 3,201,148 A | 8/1965 | Louis |
| 3,466,065 A | 9/1969 | Acker et al. |
| 3,984,133 A | 10/1976 | Bird |
| 4,019,512 A | 4/1977 | Tenczar |
| 4,457,749 A | 7/1984 | Bellotti et al. |
| 4,467,749 A | 8/1984 | Maeda |
| 4,895,570 A | 1/1990 | Arkin |

(Continued)

FOREIGN PATENT DOCUMENTS

| | | |
|---|---|---|
| DE | 2843281 C2 | 12/1983 |
| EP | 0256640 A2 | 2/1988 |
| GB | 2059268 A | 4/1981 |

OTHER PUBLICATIONS

Extended European Search Report for Application No. 16812657.1, dated Feb. 4, 2019, 10 pages.

(Continued)

*Primary Examiner* — Aaron M Dunwoody
(74) *Attorney, Agent, or Firm* — Merchant & Gould P.C.

(57) ABSTRACT

A protective guard for a medical tubing connector includes a ring, at least one flexible member attached at a first end to the ring and having a second end, and a base attached to the second end of the at least one flexible member. The ring is configured to fit over a first connection member of the medical tubing connector, while the base is configured to fit over a second connection member of the medical tubing connector. When coupled with the medical tubing connector, the protective guard helps prevent a user from touching the medical tubing connector.

4 Claims, 19 Drawing Sheets

(56) References Cited

U.S. PATENT DOCUMENTS

| | | | |
|---|---|---|---|
| 5,385,372 | A | 1/1995 | Utterberg |
| 5,688,254 | A | 11/1997 | Lopez |
| 5,957,898 | A | 9/1999 | Jepson |
| 6,234,538 | B1 | 5/2001 | Lauer |
| 6,814,726 | B1 | 11/2004 | Lauer |
| 8,585,096 | B2 | 11/2013 | Schnell et al. |
| 8,721,619 | B1 * | 5/2014 | Mobassery ............ A61M 39/20 604/905 |
| 9,726,314 | B2 | 8/2017 | Py |
| 2006/0157971 | A1 | 7/2006 | Baldwin et al. |
| 2007/0017583 | A1 | 1/2007 | Fangrow, Jr. |
| 2007/0161952 | A1 | 7/2007 | Faries et al. |
| 2007/0260189 | A1 | 11/2007 | Shaw et al. |
| 2008/0103487 | A1 | 5/2008 | Miyasaka |
| 2008/0132876 | A1 | 6/2008 | Felt |
| 2008/0287920 | A1 | 11/2008 | Fangrow et al. |
| 2010/0013215 | A1 | 1/2010 | Werth |
| 2010/0292673 | A1 | 11/2010 | Korogi et al. |
| 2012/0016318 | A1 | 1/2012 | Hoang et al. |
| 2014/0276651 | A1 | 9/2014 | Schultz |
| 2017/0252551 | A1 | 9/2017 | Schlitt et al. |
| 2018/0058618 | A1 | 3/2018 | Walterspiel |

OTHER PUBLICATIONS

International Search Report and Written Opinion for PCT/US2016/047058, dated Oct. 14, 2016, 10 pages.
Leon et al., "Antiseptic chamber-containing hub reduces central venous catheter-related infection: a prospective, randomized study," Crit Care Med. May 2003;31(5):1318-1324.
Linares, "Pathogenesis of catheter sepsis: a prospective study with quantitative and semiquantitative cultures of catheter hub and segments." J Clin Microbiol. Mar. 1985; 21(3): 357-360.
Salzman et al., "A prospective study of the catheter hub as the portal of entry for microorganisms causing catheter-related sepsis in neonates." J Infect Dis. Feb. 1993; 167(2):487-940.
Miller et al., "Comparison of the sterility of long-term central venous catheterization using single lumen, triple lumen, and pulmonary artery catheters." Crit Care Med. Aug. 1984; 12(8):634-637.
Tenny et al., "Adherent microorganisms on lumenal surfaces of long-term intravenous catheters. Importance of Staphylococcus epidermidis in patients with cancer," Arch Intern Med. Oct. 1986; 146(10):1949-1954.
Walterspiel, "Protective Ribs for Male Connectors," Infection Control & Hospital Epidemiology. Aug. 1988;9(8):342-343.
Walterspiel, "Protective ribs for connectors." Infection Control & Hospital Epidemiology. Nov. 1986;7(11):564-564.
QOSINA catalog, dated 2012, 4 pages.
International Search Report and Written Opinion for Application No. PCT/US21/49937 dated Jan. 18, 2022.

* cited by examiner

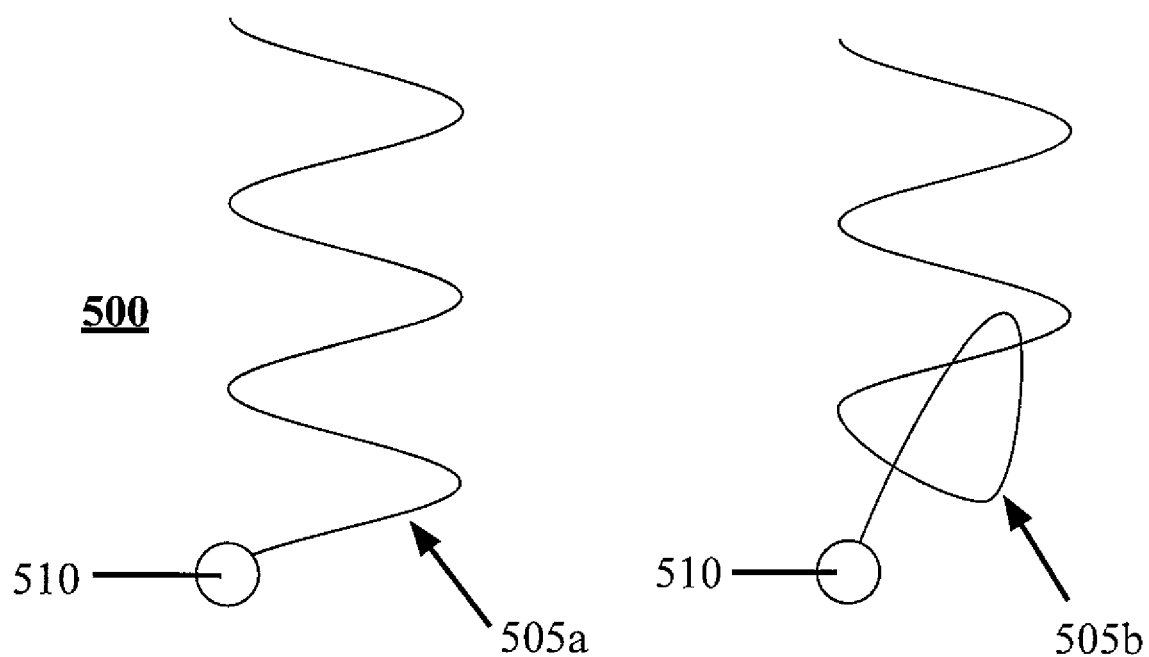
FIG. 5A  FIG. 5B
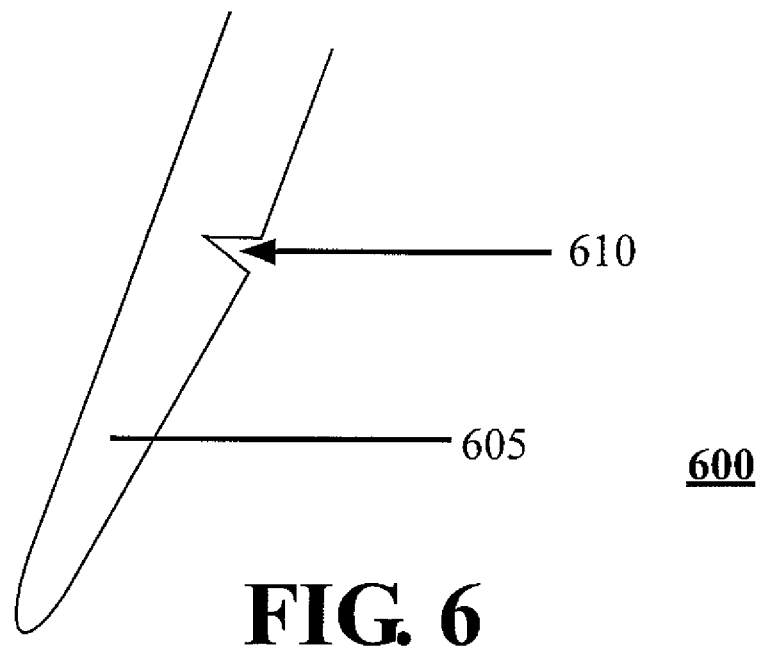
FIG. 6

1400

TUBING CONNECTOR FOR DECREASED CONTAMINATION

CROSS-REFERENCE TO RELATED APPLICATIONS

This application is a continuation of, and claims priority to U.S. patent application Ser. No. 17/018,462, filed on Sep. 11, 2020, which is a continuation-in-part of, and claims priority to U.S. patent application Ser. No. 15/789,388, filed on Oct. 20, 2017, which is a continuation of, and claims priority to PCT Patent Application No. PCT/US2016/047058, filed on Aug. 15, 2016, which claims priority to U.S. Provisional Patent Application No. 62/180,201, filed Jun. 16, 2015. All of the above-referenced patent applications are hereby incorporated herein by reference.

FIELD OF THE DISCLOSURE

The present disclosure relates to medical and scientific devices. More particularly, the present disclosure relates to connectors and protective devices for helping prevent contamination of connectors of medical or scientific devices, such as tubes connected by a luer-type or male/female connector.

BACKGROUND

Standard connectors and other male-to-female and female-to-male connectors are used to connect tubes and syringes for the delivery of sterile fluids or gases. These connectors typically have a male element that is inserted into a female element, with such couplings then reversibly secured by various screw-on and locking devices.

Human skin is colonized by a microbiome, or a mixture of colonizing microbes that typically includes coagulase negative staphylococci, which are the most common agents found to cause infections of indwelling catheter lines. Skin colonizing microorganisms can also comprise *Staphylococcus aureus*, a vast array of Gram-negative organisms, yeast, and fungi. Many of these microorganisms exhibit resistance to one or multiple antimicrobial agents and have become very difficult to treat.

Similarly, connections between tubes or conduits connecting ventilators to patients are potential locations for contamination. Because ventilators often have water vapor that may condense on connectors, tubes, and conduits, bacterial and other undesirable organisms may colonize ventilator components, thereby causing increased morbidity and mortality.

Similar tube connectors are also used in the biotechnology industry, cell culture, and laboratory technologies. It would be advantageous to maintain a sterile conduit for fluids in such applications as well.

Pathogenic organisms adhere easily to any protruding or otherwise exposed elements of standard intravenous lines and a variety of other male-to-female connectors, as well as to needle injection ports and needleless injection ports. Accidentally caught microorganisms can grow into a biofilm, whose formation is aided by the fluid filled capillary spaces that are formed when a fluid coupling is made. Free swimming (planktonic) organisms are released from such biofilms. They are carried into the bloodstream, colonize the inner surfaces of indwelling catheters and the clot(s) that invariably form at the end of infusion lines.

The colonization, clotting, and the inflammatory responses to these organisms cause catheter occlusions, emboli, signs and symptoms of inflammation, seeding into organs, and prompt diagnostic dilemmas, which lead to various diagnostic and therapeutic interventions. Apart from the avoidable human suffering caused, these contaminations increase healthcare costs significantly.

Therefore, it would be advantageous to have improved connectors for tubular devices for use in medicine, biotechnology and other scientific uses.

SUMMARY

In an embodiment, the sterile male element of a connector usually protrudes beyond a securing element (also referred to as a "part" or a "portion") of the connector to ease the insertion into the female counterpart of a connector. This functional advantage is offset by the disadvantage of the protruding male or female element being exposed to accidental contact with non-sterile environmental surfaces that include the skin of a patient or the caregiver, furniture, clothing and the like. This risk of avoidable colonization and infection also pertains to all freely exposed parts of female insertion couplings (also referred to as "hubs") and the needle, as well as needleless injection ports that frequently have valves or membranes and are particularly prone to colonization with pathogens that subsequently cause line and catheter infections.

Because U.S. healthcare providers are no longer being paid to treat nosocomial infections that could have been prevented, there is now a strong incentive for the modification of design of long-held and well-known connectors. This incentive also extends to home health care home self-care.

The passive protective devices or guards of this disclosure address these economic and healthcare problems by reducing or preventing healthcare associated infections. Protective guards can include flexible elements or "ribs" that extend outwards from the connector element and also extend beyond the distal (open) end of a male or female luer connector element. When in use, these protective guards may make contact with a source of contamination but will keep the critical ends of the connectors from making contact with the source of contamination.

In certain embodiments, a guard may be made with flexible protective ribs or resilient fibers that can be moved from a relaxed position by forces used to connect complementary elements of a connector. In certain embodiments, a guard can be a solid element that can be fitted to a device. Even if a connection is not completed, and the connector elements must be re-engaged, the flexible protective guard can help maintain sterility of the device, and thereby decrease the likelihood of inadvertent contamination of the device and the patient. In certain embodiments, a guard is axially compressible to allow for swabbing of these connector elements.

In another aspect of the present disclosure, a protective guard for a medical tubing connector may include a ring, at least one flexible member attached at a first end to the ring and having a second end, and a base attached to the second end of the at least one flexible member. The ring is configured to fit over a first connection member of the medical tubing connector, while the base is configured to fit over a second connection member of the medical tubing connector. When coupled with the medical tubing connector, the protective guard helps prevent a user from touching the medical tubing connector. The protective guard also typically helps prevent the medical tubing connector from touching various surfaces and objects (moving and non-moving) in the environment.

In some embodiments, the ring comprises a convex outer surface. In some embodiments, the at least one flexible member includes multiple flat, flexible members configured to preferentially flex outward when the protective guard is compressed longitudinally. In some embodiments, the at least one flexible member includes a spring. In such embodiments, the base may be a final coil of the spring at an the second end. In some embodiments, the base is a cylinder. The medical tubing connector may be a luer connector including a male component and a female component that fit together.

In another aspect of the present disclosure, a protective guard for a medical tubing connector may include a cylindrical base and a curved shield extending laterally away from the base and beyond and around one end of the base. The cylindrical base is configured to fit over a first connection member of the medical tubing connector, and the curved shield is configured to curve around an end of the first connection member. When coupled with the medical tubing connector, the protective guard helps prevent a user from touching the end of the first connection member. The protective guard also typically helps prevent the medical tubing connector from touching various surfaces and objects (moving and non-moving) in the environment.

In some embodiments, the protective guard further includes two wings extending from the base to facilitate handling of the protective guard by the user. In some embodiments, the protective guard further includes an orienting feature on the curved shield to indicate an orientation of the curved shield to the user.

In another aspect of the present disclosure, a method for connecting two fluid transmitting devices to each other while protecting the fluid transmitting devices from contamination may involve coupling a connector guard with a first connector component at one end of a first fluid transmitting device without touching an end of the first connector component, holding the first connector component via the connector guard, and attaching a second connector component at one end of a second fluid transmitting device to the first connector component without touching at least the first connector component. The connector guard at least partially surrounds at least part of the first connector component and the second connector component when the first and second connector components are attached to one another.

Examples of types of fluid transmitting devices include but are not limited to gas delivery devices, intravenous lines, and other medical tubing. In some embodiments, coupling the connector guard with the first connector component involves placing a ring of the connector guard over the first connector component, where the ring is coupled with at least one flexible member attached at a first end to the ring and having a second end attached to a base attached of the connector guard, and wherein the base resides over the second connector component when it is attached to the first connector component. Alternatively, coupling the connector guard with the first connector component may involve placing a base of the connector guard over the first connector component, such that a curved shield extending laterally away from the base and beyond and around one end of the base protects the end of the first connector component. Such a method may optionally further involve bending the curved shield to expose the end of the first connector component before attaching the first connector component to the second connector component. The method may also involve resting the second connector component in a groove on the shield of the connector guard.

These and other aspects and embodiments are described in further detail below, in reference to the attached drawing figures.

BRIEF DESCRIPTION OF THE DRAWINGS

This disclosure is described with reference to specific embodiments thereof. Other features can be appreciated with reference to the figures, in which:

FIG. 5A depicts is a side view of a protective rib of undulant protective shape, according to one embodiment;

FIG. 5B is a side view of a protective rib as shown in FIG. 5A, with the rib bent to increase coverage area to the side and flexibility, according to one embodiment;

FIG. 6 is a side view of a guard having slanted rib with a bending or breaking point, according to one embodiment;

DETAILED DESCRIPTION

Figure 1:
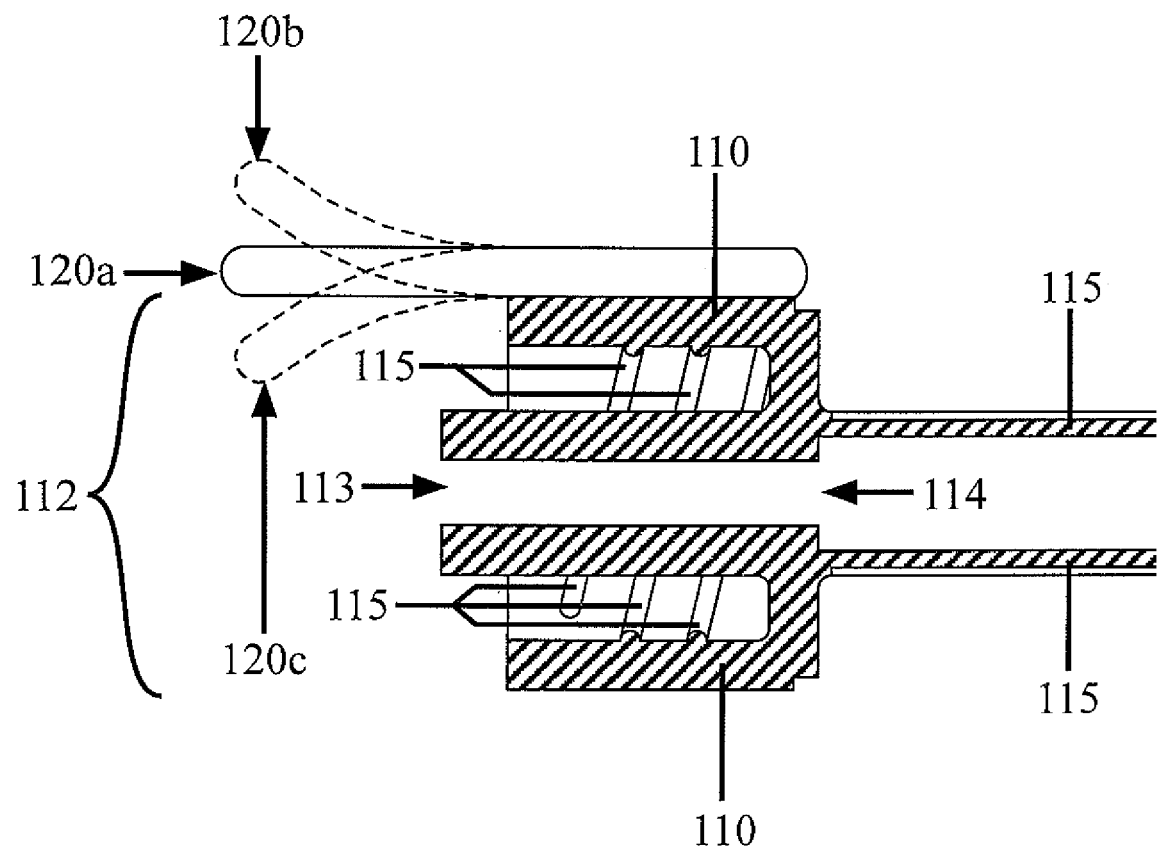
FIG. 1 is a side view/longitudinal section (or cut through) of a male luer lock (bottom) and a protective guard element or rib, according to one embodiment.

This disclosure includes some well-known terms and others that are defined below.

The term "connector" means a device used to connect tubing together.

The term "element" means a part of a device.

The term "connector part" or "luer part" means either a male or female element.

The term "luer" or "Luer" means a device for connecting two devices together to provide a central channel, through which a fluid or gas can flow between the devices. The term "luer" is not intended to be solely for use in intravenous lines, but also includes any connector where sterility of the interior of the device is desired. The term "luer" includes any connector used to couple fluid carrying devices.

The term "male" means an element or part of a connector having a protruding end sized and adapted to fit with a counterpart "female" element.

The term "female" means an element or part of a connector having a receiving element sized and adapted to accommodate a "male" element.

The term "guard" or "protector" means a device affixed to an element that extends laterally, distally, or both laterally and distally beyond the end of an element to provide a shield to hinder a male or female element from making unintended contact with a source of potential contamination.

The term "fiber" or "rib" means a resilient element that alone or in combination with other fibers or ribs can form a guard.

The term "cage" means a configuration of a guard having a network of interdigitated or interlocking ribs, or a configuration produced by molding resilient materials into a non-rigid but solid shape.

Connectors of this disclosure include an outer addition to existing intravenous or gas line connectors and couplings. The new couplings of this disclosure provide passive prevention of avoidable healthcare associated infections, specifically of intravenous lines, catheter infections that follow catheter hub colonization, or respirators. (1. DE 2843281 A1 Oct. 4, 1978 Apr. 10, 1980; 2. Linares J., Sitges-Serra A, Garau J., et al., Pathogenesis of catheter sepsis: a prospective study with quantitative and semiquantitative cultures of catheter hub and segments. J. Clin Microbiol 1985; 21:357; 3. Tenney J H Moody M R, Newman K A, et al., Adherent microorganisms on luminal surfaces of long-term intravenous catheters. Importance of *Staphylococcus epidermidis* in patients with cancer. Arch Intern Med 1986; 146:1949; 4. Miller J J, Venus B, Mathru M., Comparison of the sterility of long-term central venous catheterization using single lumen, triple lumen, and pulmonary artery catheters. Crit. Care. Med. 1984; 12:634; and 5. Salzman M B, Isenberg H D, Shapiro J F, et al., A prospective study of the catheter hub as the portal of entry for microorganisms causing catheter-related sepsis in neonates. J. Infect. Dis. 1993; 167:487), but their application also includes chest tubes, gas lines, urinary drainages and all post-surgical or interventional drainages and includes needle and needleless access ports.

Embodiments of the disclosure include improved designs that build upon known protective devices, including protective guards, rib elements and extensions, such as those described in patent DE3816191A1 and related publications (6. Leon C. Alvarez-Lerma F., Ruiz-Santana S., et al, Antiseptic chamber-containing hub reduces central venous catheter-related infection: a prospective, randomized study. Crit. Care. Med. 2003; 31:1318; 7. Walterspiel, J N, Protective Ribs for Male Connectors. Inf. Control and Hospital Epidemiology 1988: 9(8): 342; 8. Walterspiel, J N, Protective Ribs for Connectors, Inf. Control and Hospital Epidemiology 1986; 7(11): 564). Protective guards and extensions on fluid or gas couplings can now, by design, be compressed, bent outwards and/or broken off during the process of closing and securing a coupling. The protective guards are configured to stay out of the way of closing and securing a connection, regardless of the make, shape or form of the respective counter connector or coupling and its securing provisions.

An embodiment includes a connector having a guard made of a resilient, pliable, and easily bendable material, compared to the solid and rigid materials that medical grade couplings are made of. An embodiment may comprise a resilient material having indentations and/or thinner parts that allow the resilient material to bend, and combinations of both resilient and rigid materials. Guards, by virtue of their composition and/or design can be easily bent away from or around a counter connector part that may be in the way during secure closing of a connector.

Referring to FIG. 1, a schematic rendering of such a bending embodiment of a guard having a protective rib is depicted. FIG. 1 depicts a schematic longitudinal section 100 through a male end of a luer connector 112 of this disclosure, which includes a body element 110 having a series of diagonal threads 115, thereby forming male luer connector 112 having a distal end 113 and a proximal end 114. Proximal end 114 is connected to tube 105. Flexible rib 120a of a guard is shown in its relaxed position. The rib is depicted bent away from 120b, or towards 120c, or around the axis (not shown) from the male luer connector 112.

An embodiment of a guard having two or more protective ribs can be made of a resilient, pliable, and/or easily bendable material. This material may be distinguished from the solid materials that medical grade couplings are made of. Alternatively or additionally, the guard may include indentations and/or a thinner element that can allow it to bend. Guards having protective ribs, by virtue of their composition and/or design can be easily bent away from any counter connector parts that may be in their way during the secure closing of a connector. A guard may include one or more ribs mounted on a circular rotating ring shaped in repeating S forms that can form a receiving opening funnel.

Resilient, flexible materials for guards and ribs may include pliable plastics, such as polyvinyl chloride (PVC) having various amounts and kinds of high and low molecular plasticizers that can include phthalates, polyethylene (PE), and can include various forms and mixtures such as ultra-high-molecular-weight polyethylene, cross-linked polyethylene, medium-density polyethylene, linear low-density polyethylene, low-density polyethylene, very-low-density polyethylene, chlorinated polyethylene and copolymers, polypropylene (PP) in its various forms, including polypropylene glycol (PPG), silicone elastomers in its various forms, including cross-linked polydemethylsiloxane, fluoroplastics, polystyrene, polyethylene terephthalate (PET) and other types of plastics and combinations. Materials may be transparent and/or colored materials that fulfill the sterility, sterilizability, visibility, and flexibility requirements for said protectors. The material for the protectors, their clip-on embodiments, and their parts can also include metals, specifically non corrosive alloys. The surfaces can have a hydrophobic coating and color coding.

Figure 2:
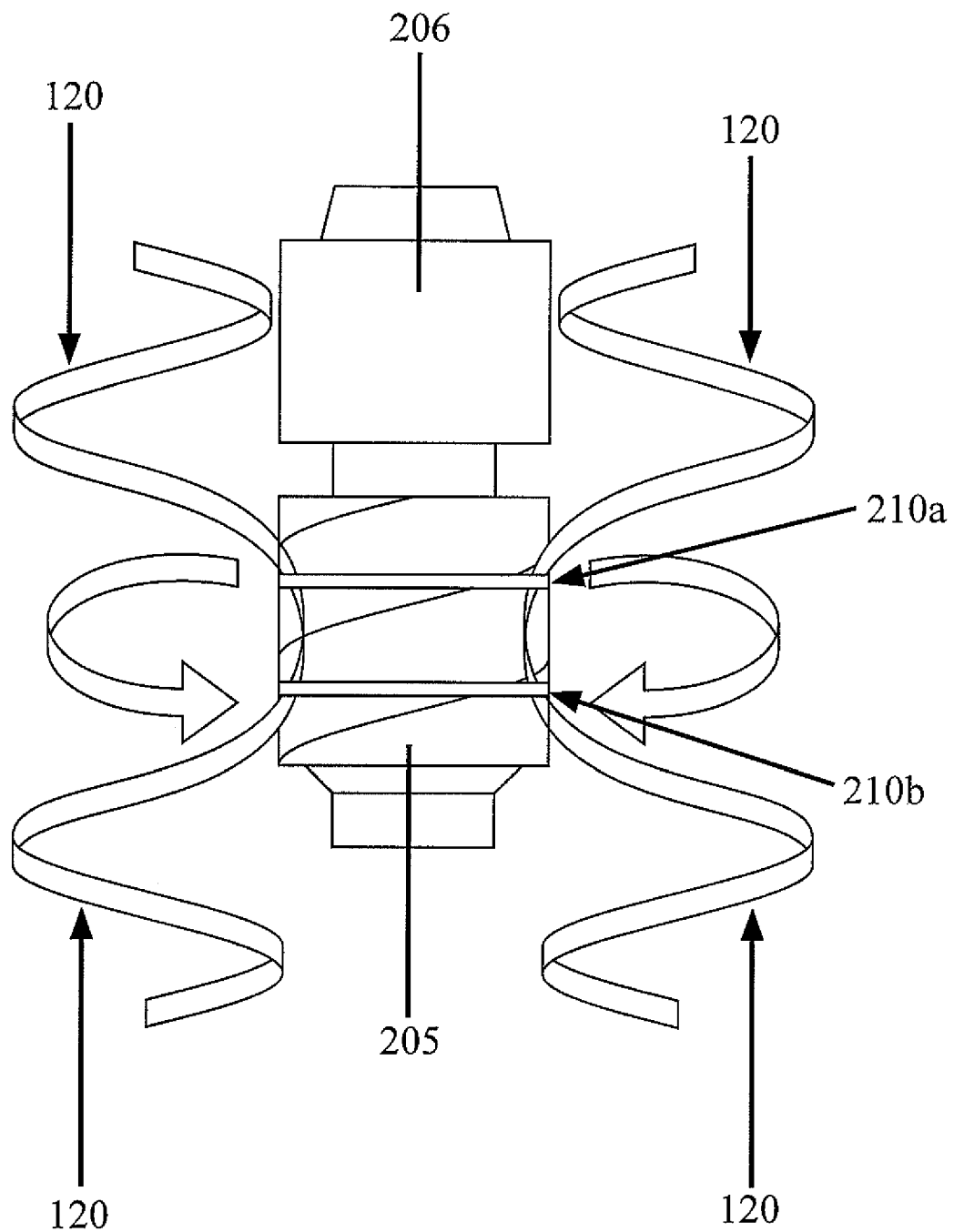
FIG. 2 is a schematic drawing of bending ribs or guards of a shape that by a circular arrangement or assembly of multiple ribs for receiving funnel or guard, according to one embodiment.

FIG. 2 is a schematic drawing of a receiving funnel embodiment, which includes a male-female connector having two protective ribs 120a, pointing into their respective distal and proximal directions arranged around a typical luer lock-type coupling extender that has a male part 205 below and a female part needleless coupling part 206 above. Shown in FIG. 2 in schematic form are also rotating rings 210a and 210b, on which a rib assembly can rotate (arrows), for the ribs to easily fit into protective assemblies on a counter coupling.

Figure 3:
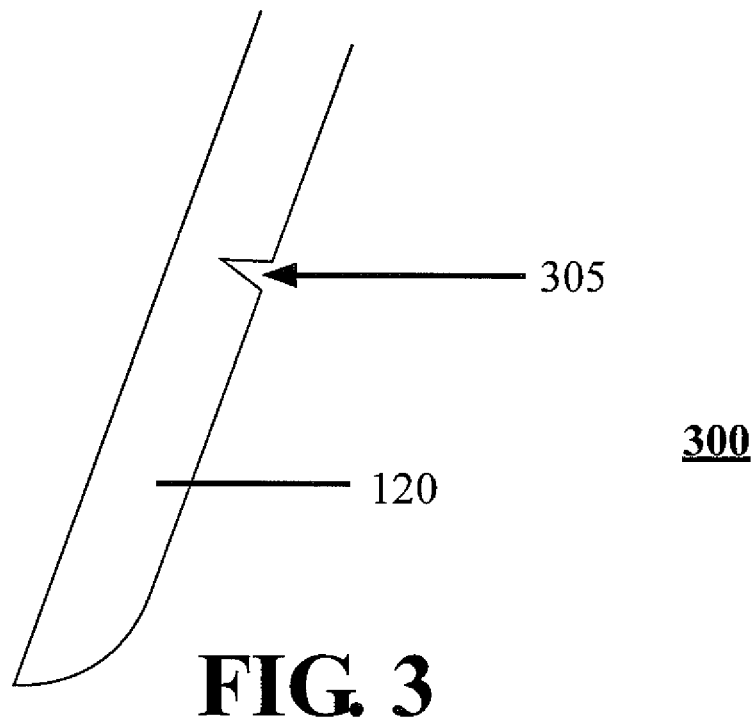
FIG. 3 is a side view of a protective rib with one bending or breaking point, according to one embodiment.

FIG. 3 depicts a schematic drawing 300 of an embodiment showing the distal end of rib 120a. Proximal to the distal end, groove 305 is shown. When rib 120a is deflected away from the Luer connector, it can break at groove 305.

Figure 4:
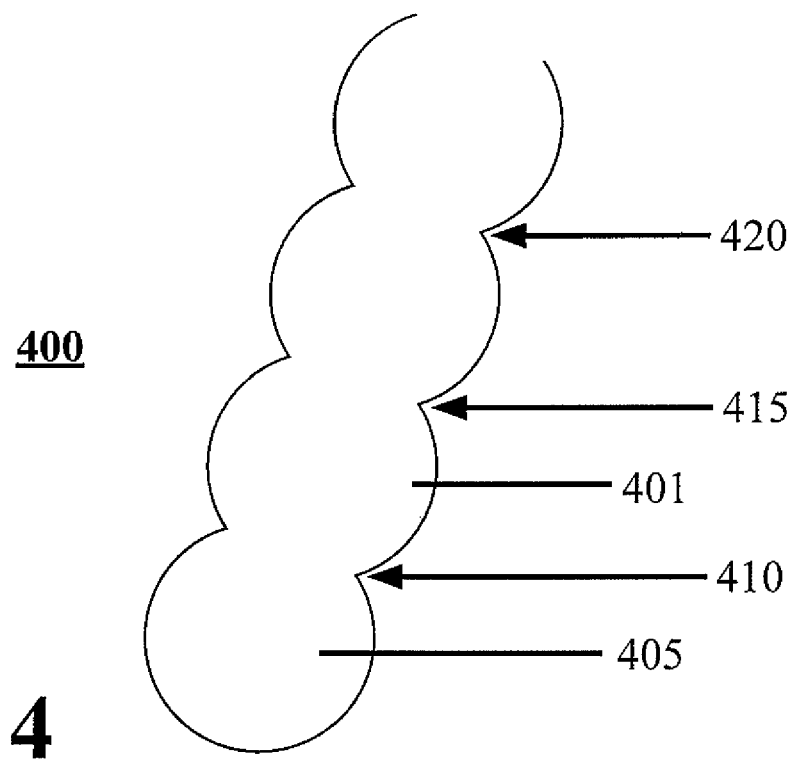
FIG. 4 depicts is a side view of a protective rib with repetitive variations in thickness or diameter along its length that create several bending or breaking points, according to one embodiment.

Referring now to FIG. 4, one embodiment may include protective ribs forming a chain or series of globular or ovoid elements that are connected by thinner areas that can bend and/or break away when coming in contact with a counterpart connector part that may be in their way during the closing of a coupling. Globular or ovoid forms of the elements and combinations thereof can facilitate the slip-over and rotation-over protruding parts of a counter-coupling. A schematic drawing of a rib of such an embodiment is depicted in FIG. 4, which shows an embodiment 400 with a rib 401 with multiple indentations 410, 415, and 420.

Referring now to FIGS. 5A and 5B, one embodiment of a protective rib cage comprises two or more protecting ribs of undulant shape that can be compressed and/or bend inwards or outwards when the coupling parts are positioned, to or intertwined with each other during the process of closing and securing a luer connector. FIG. 5A depicts an embodiment 500 having a rib 505a in a relaxed state. Element 510 is a looped ending of rib 505a, to facilitate sliding over protrusions on a counterpart. Such looped ends 510 of a rib 505a can more easily move out of the way of a protrusion than can a simple pointed end.

FIG. 5B illustrates a rib 505b that is deflected to increase its peripheral coverage area. The rib 505a includes the looped end 510 at its distal end to facilitate sliding over or around protrusions.

Referring now to FIG. 6, in some embodiments, a protective rib cage may include two or more protecting ribs with bending and/or breakpoints whose inner surfaces are slanted at an outward angle, so that said rib, in aggregate, form a funnel with the individual ribs being bent out or even breaking off when the funnel is pried open under the gliding pressure over impeding parts of the counter connecting coupling. An example of a rib in such an embodiment is depicted in FIG. 6.

FIG. 6 is a schematic drawing of an embodiment 600 having a slanted rib 605. The distal end of rib 605 is slanted to more easily fit over a complementary connector part. Proximal to the distal end of rib 605, a groove 610 is shown. When two complementary elements of a luer connector (i.e., male and female), rib 605 may break at groove 610. A guard may include two or more of such slanted ribs 605, to form a funnel that opens when encountering an impediment upon the closing of a connection.

Figure 7:
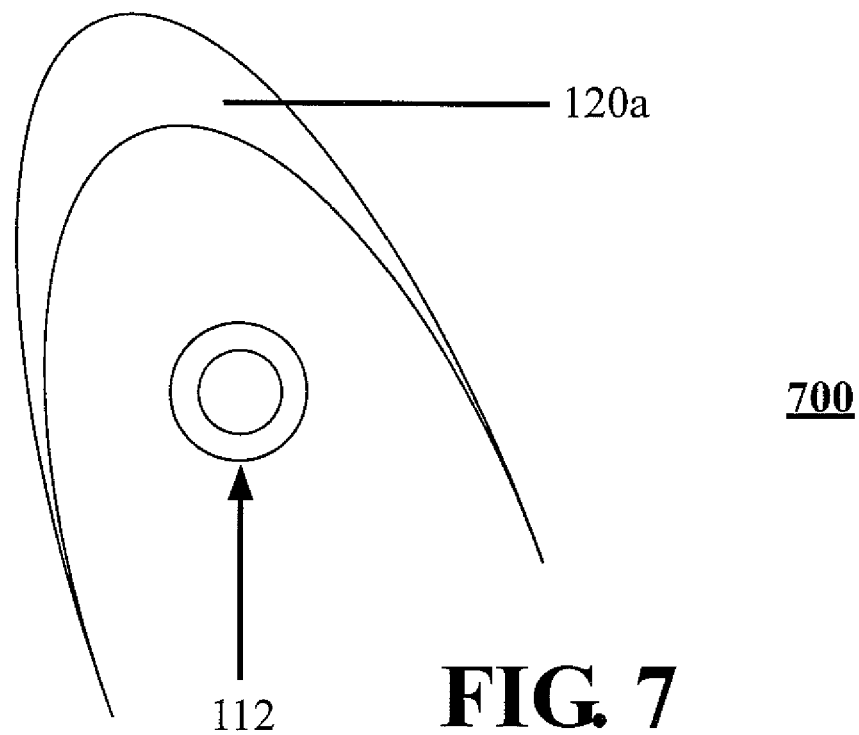
FIG. 7 is a perpendicular cross-sectional view cut through a rib assembly with one curved rib protecting a male connector part, according to one embodiment.

FIG. 7 is a cross-sectional view of an embodiment 700 in which an element of a luer connector 112 is surrounded in part by a rib 120a, which protects the luer connector 112 and where the open element adds visibility for engagement and increased flexibility.

Figure 8:
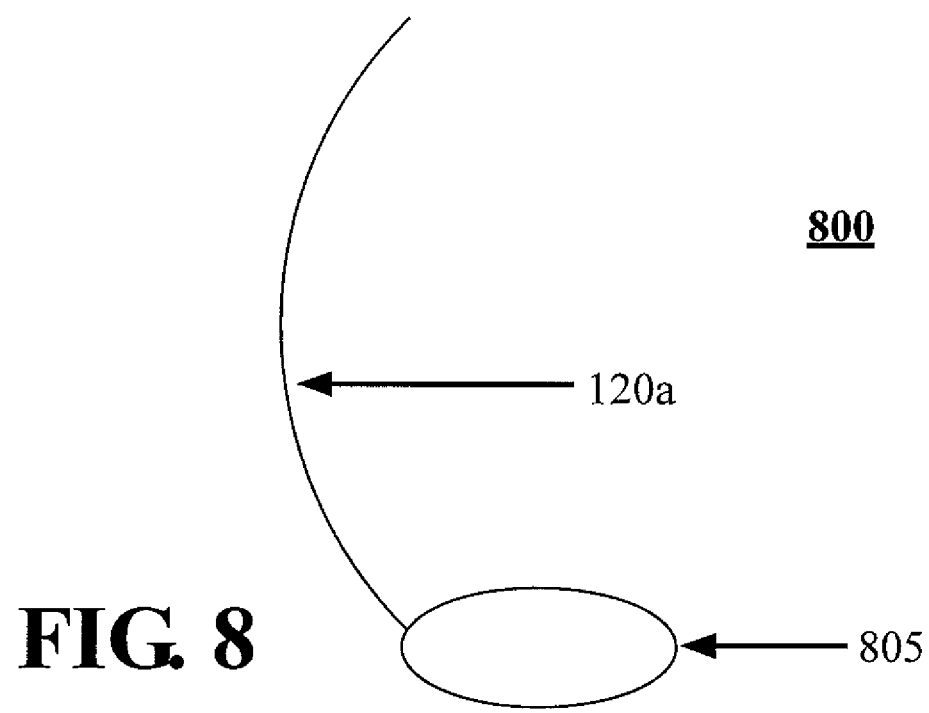
FIG. 8 is a side view of a protective rib ending in a circular protecting ring, according to one embodiment.

FIG. 8 is a schematic drawing of an embodiment 800 having a rib 120a connected to circular protecting ring 805 that fits over or under an impeding part of a counter connecting coupling or protector.

Figure 9:
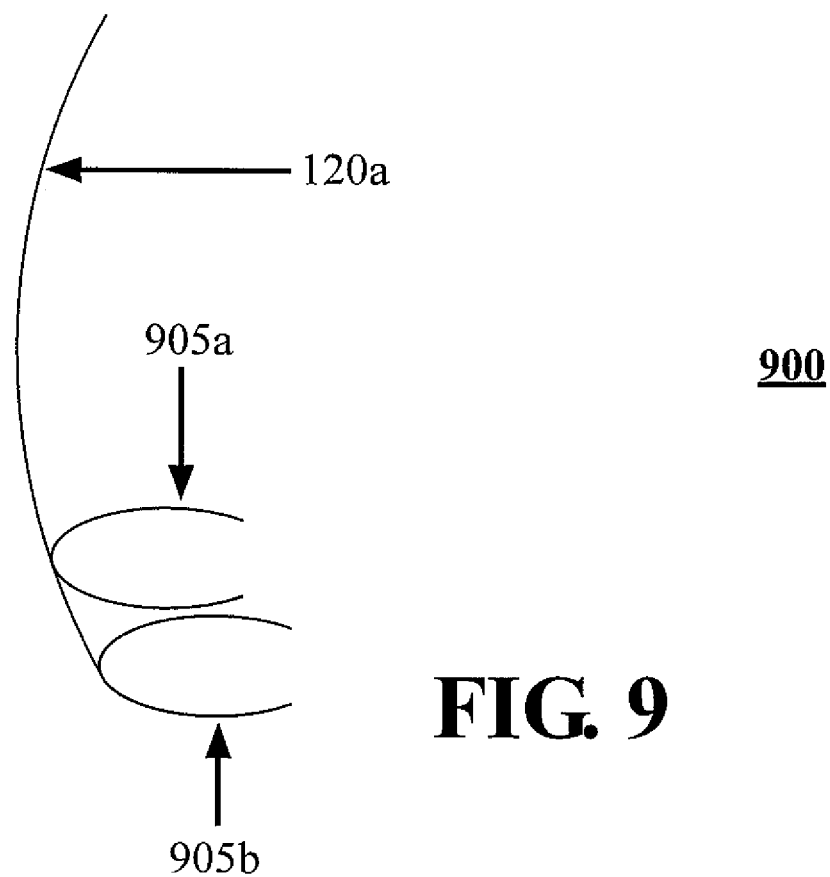
FIG. 9 is a side view of a protective rib ending in two open circular protecting rings, according to an alternative embodiment.

FIG. 9 is a schematic drawing of an embodiment 900 of a rib 120a having at a proximal element and two open circular protecting rings 905a and 905b that can fit over a counter connecting coupling or protector.

Figure 10:
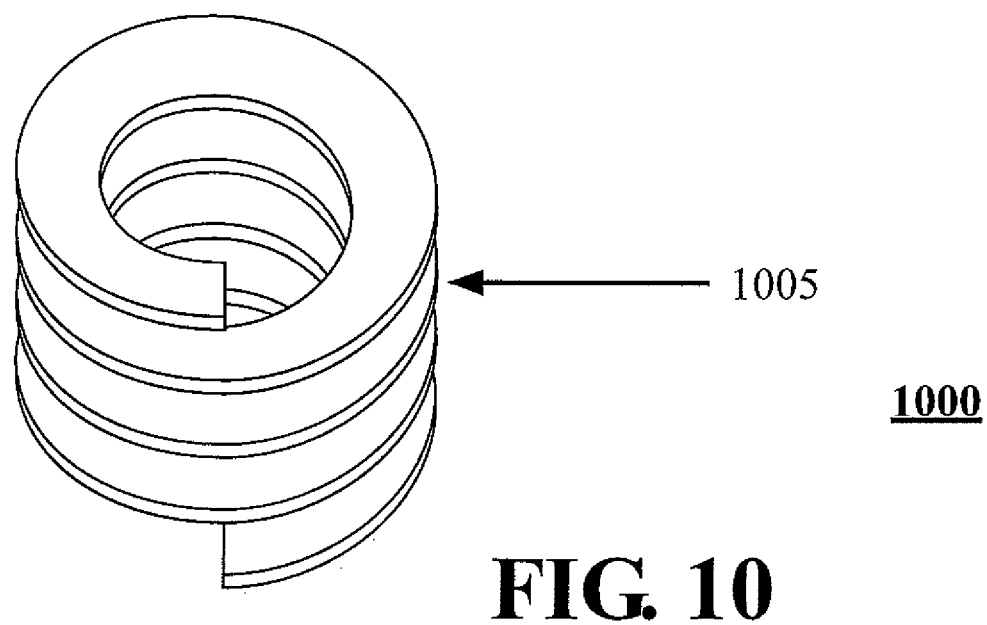
FIG. 10 is a perspective view of a protective helical guard, according to another embodiment.

FIG. 10 is a perspective view of another embodiment 1000 of a protective circular guard 1005, which can be compressed out of the way or around an impeding part during coupling. Such a circular guard 1005 can be used on a female connector element, so a guard on a male connector element can be inserted inside the circular guard 1005. A similar guard may have helical structure.

Figure 11:
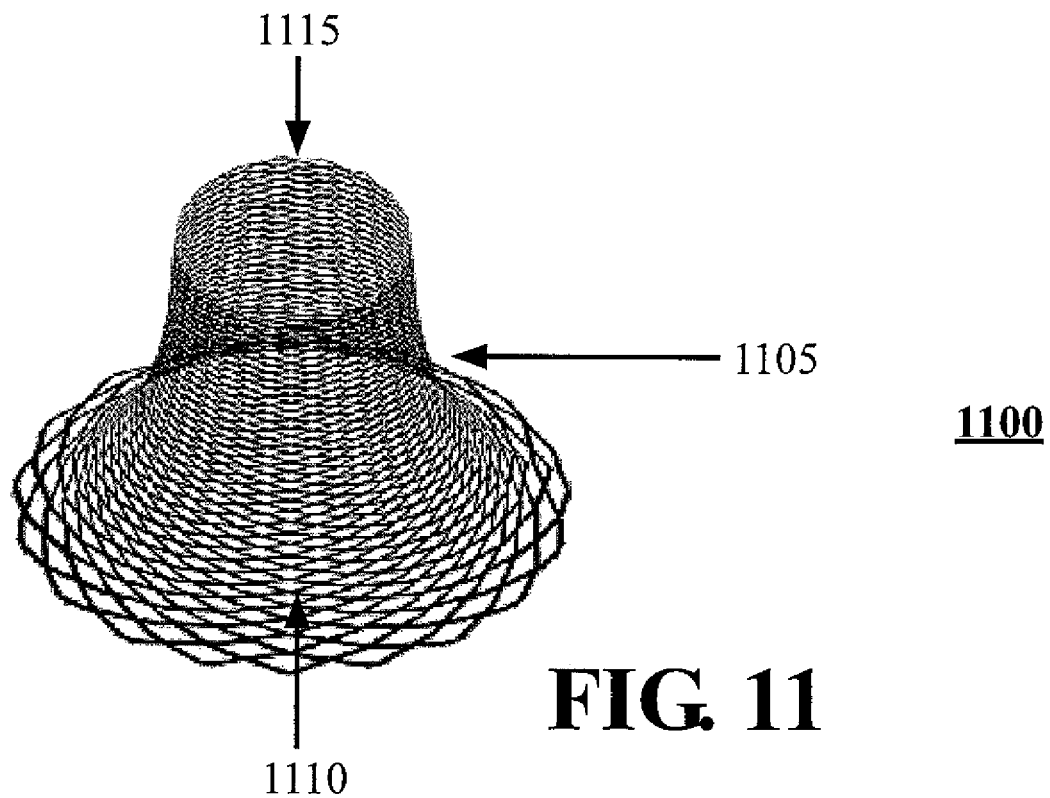
FIG. 11 is a perspective view of a protective guard with flexible, interlocking, connected and superimposed compressible spiral shaped ribs, according to one embodiment.

FIG. 11 is a perspective view of an embodiment 1100 having ribs arranged to form a funnel shaped guard 1105 having a larger diameter opening 1110 and a narrower diameter opening 1115. Narrower diameter opening 1115 can fit over a luer connector part (not shown), to hold it in place relative to the luer connector part, with the larger diameter opening 1110 providing protection for the luer element inside the cage. Such a funnel shaped guard 1105 can be placed on a female connector element and can be sized to permit a male connector element to fit within protective guard 1105.

Figure 12:
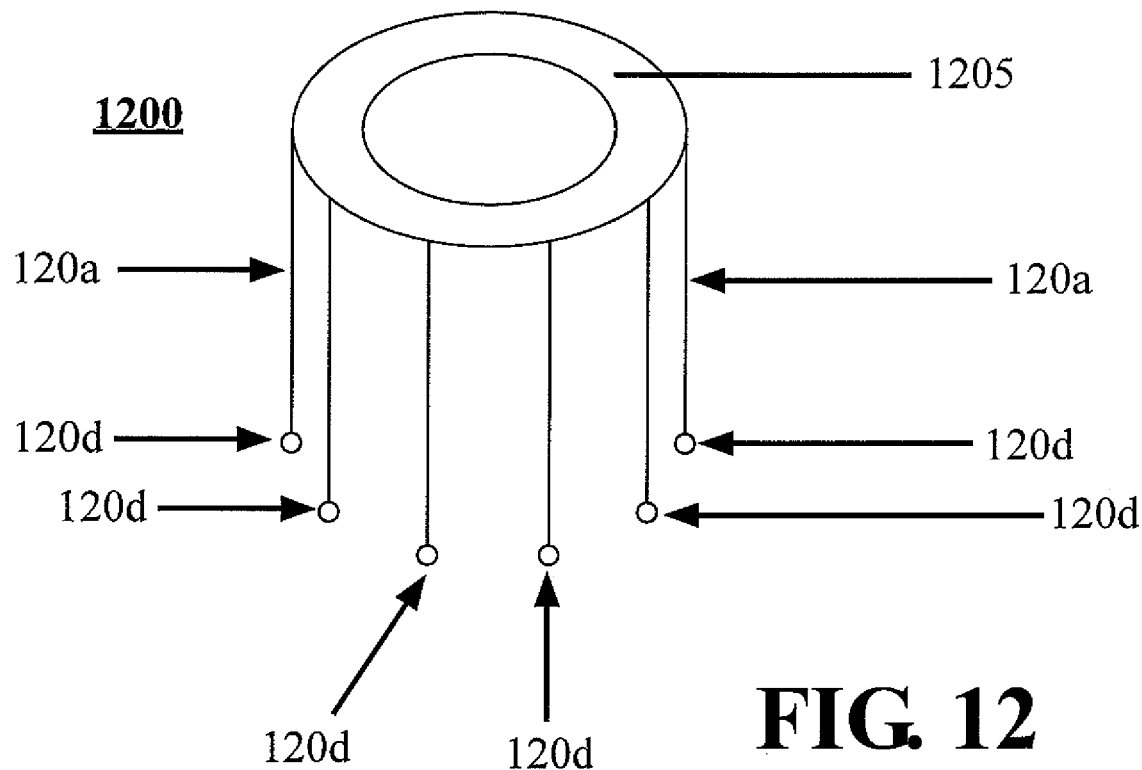
FIG. 12 is a perspective view of a protective rib assembly where ribs are arranged on ring that can be rotated in a fitting groove on a connector, according to another embodiment.

FIG. 12 is a schematic drawing of a protective rib assembly 1200, where ribs 120a are arranged on ring 1205 that can be placed in a fitting groove on a connector. End loops 120d are included at the distal ends of ribs 120a, to facilitate sliding of ribs 120a over a protrusion. Ring 1205 can be assembled with a luer connector element to be freely rotatable around the luer connecting element.

Figure 13:
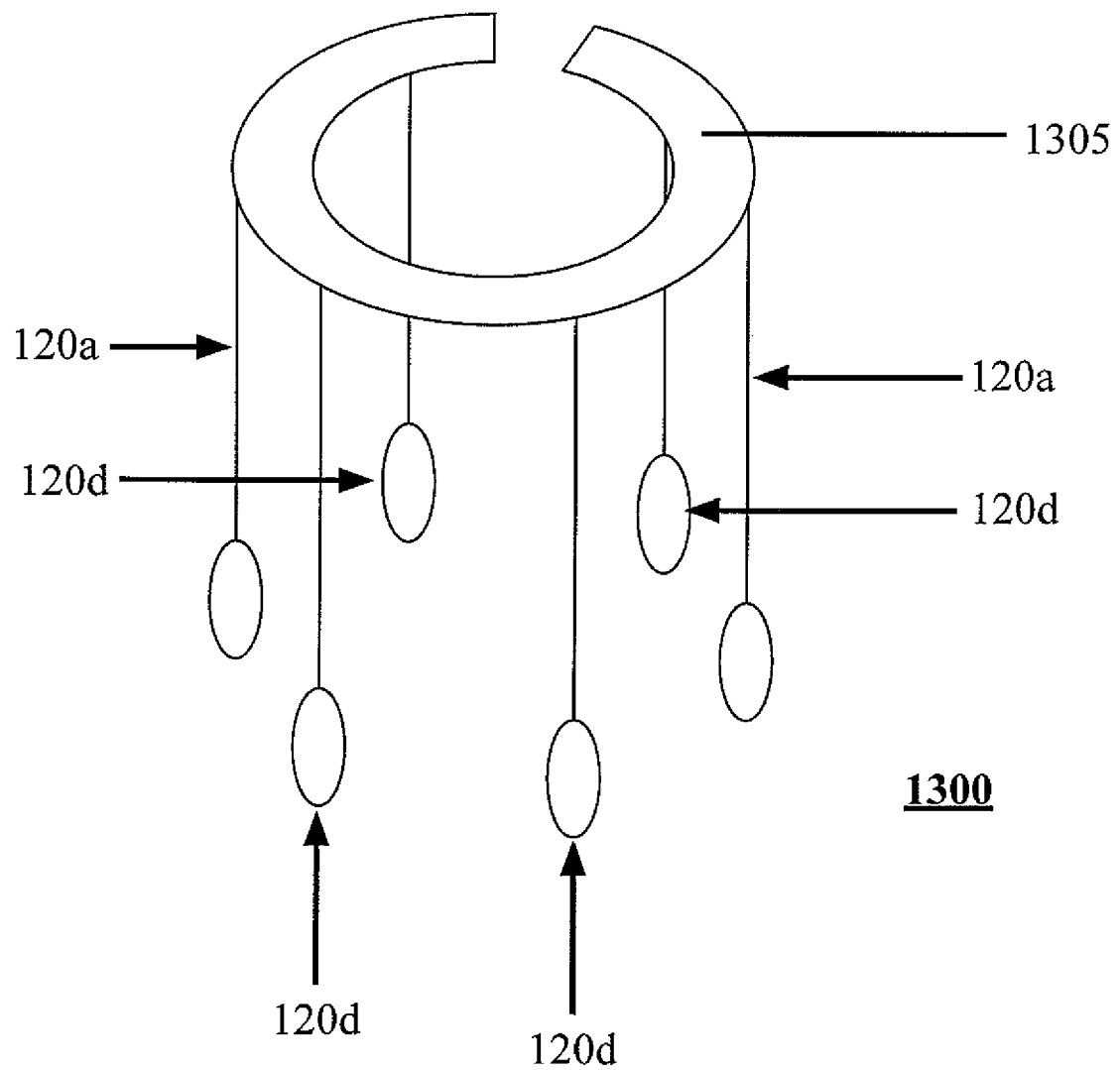
FIG. 13 is a perspective view of a protective guard with ribs having loops at their distal ends and arranged on an open ring, according to one embodiment.

FIG. 13 is a schematic drawing of another embodiment of a protective rib assembly 1300, where ribs 120a have loops 120d at their distal ends to facilitate sliding of ribs 120a over a protrusion. Open ring 1305 can be slidably affixed to a luer connector part and axially rotated. This open ring 1305 can be clipped into a fitting groove on a connector.

Figure 14A:
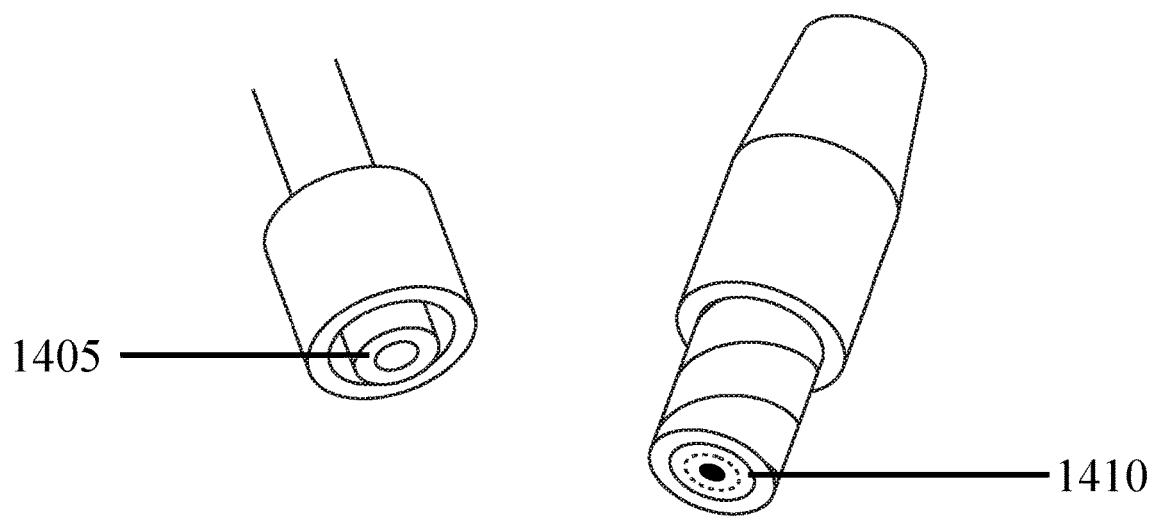
FIG. 14A is a perspective view of a male luer connector having an unprotected element and a female luer needleless connector having an unprotected element.

FIG. 14A illustrates a prior art male luer connector unprotected element 1405 and a prior art female luer needleless connector unprotected element 1410.

Figure 14B:
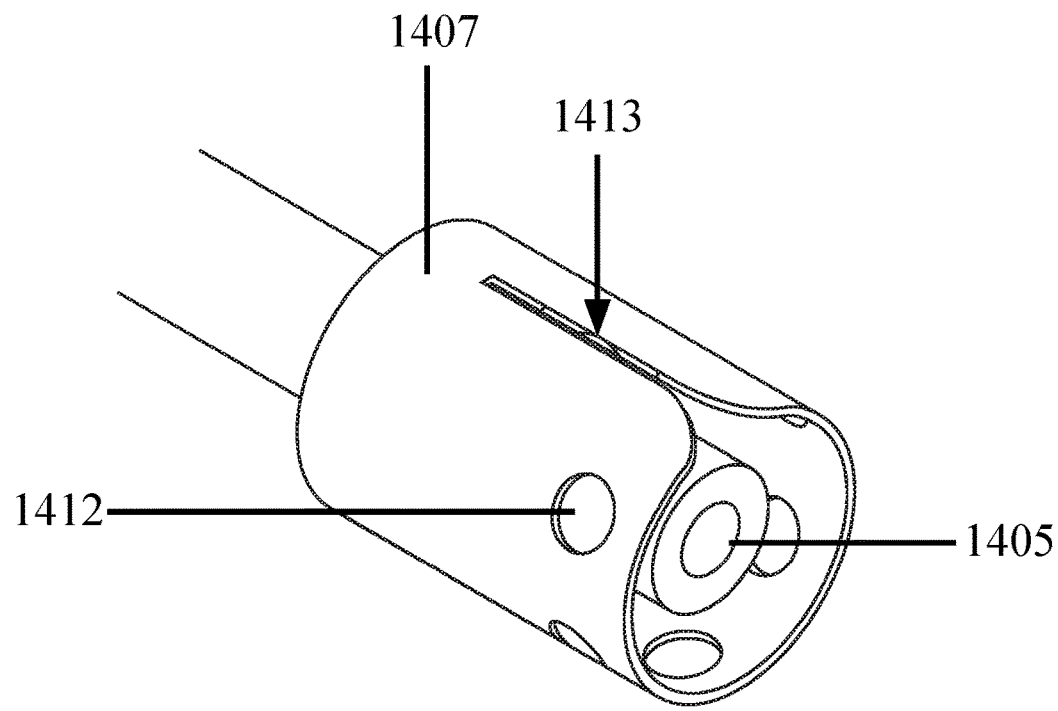
FIG. 14B is a perspective view of a "cage" guard according to one embodiment, placed over a male luer connector.

FIG. 14B illustrates another embodiment 1400, showing male luer connector element 1405 with a "cage" type protector 1407 attached. The cage type protector 1407 need not have ribs and may be manufactured as a single piece. Cage type protector 1407 is shown extending beyond the distal end of male luer connector element 1405, thereby making it less likely that the distal end of the male luer connector element 1405 will make contact with a source of contamination. Such openings can increase visibility for proper alignment with a counterpart connector element.

Figure 14C:
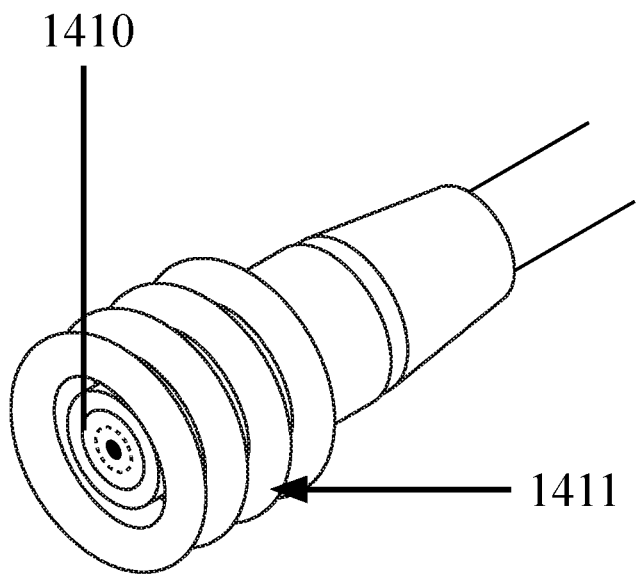
FIG. 14C is a perspective view of a female end of a needleless connector protected by a compressible circular protector, according to one embodiment.

FIG. 14C shows female luer needleless connector unprotected element 1410 protected by a compressible protector 1411, where the compressibility of protector 1411 allows for swabbing of the exposed end of element 1410. As with the "cage" type protector illustrated in FIG. 14B, circular protector 1411 extends beyond the distal end of the female luer connector element 1410, thereby making it less likely that the distal end of the female luer connector element 1410 will make contact with a source of contamination. The compressible nature of this protector 1411 facilitates cleaning of a connector part.

Figure 14D:
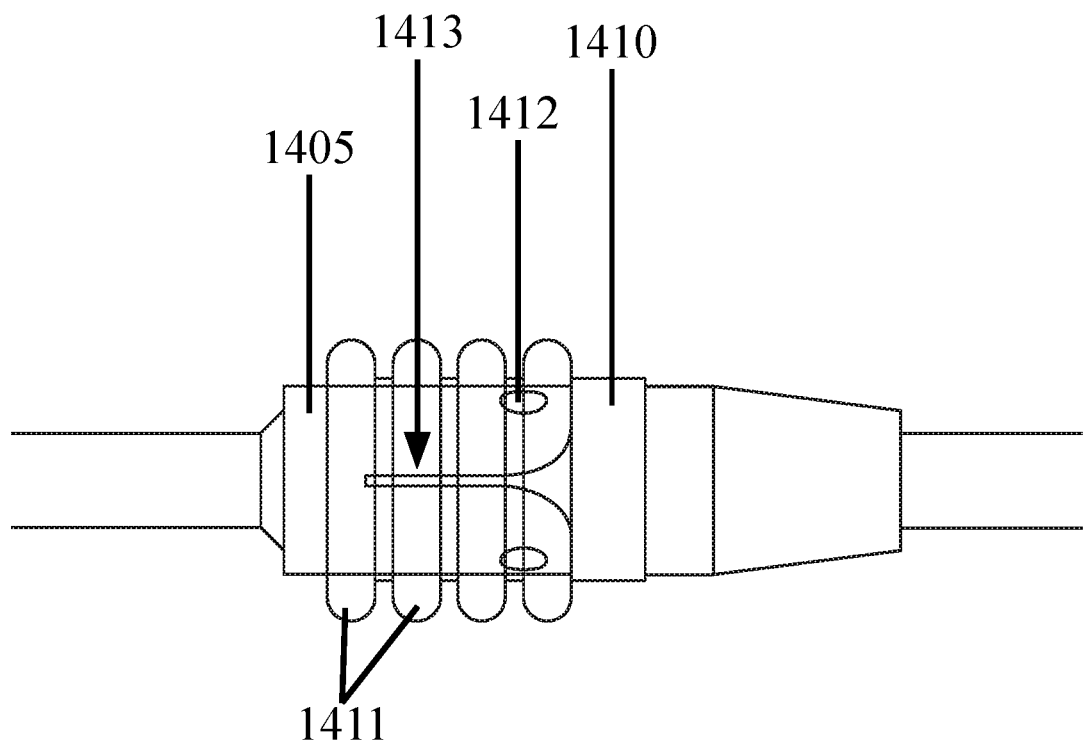
FIG. 14D is a side view of a protected luer connector with the male end and female end connected together, according to one embodiment.

FIG. 14D is a side view of the assembled components from FIGS. 14B and 14C, with male end 1405 and female end 1410 connected together. Male cage protector 1407 enclosing male end 1405 has incision 1413 on its lateral side that allows cage 1407 to have its diameter reduced (to be compressed) when sliding into female protector 1411 or its diameter increased when sliding over a protrusion.

Figure 15:
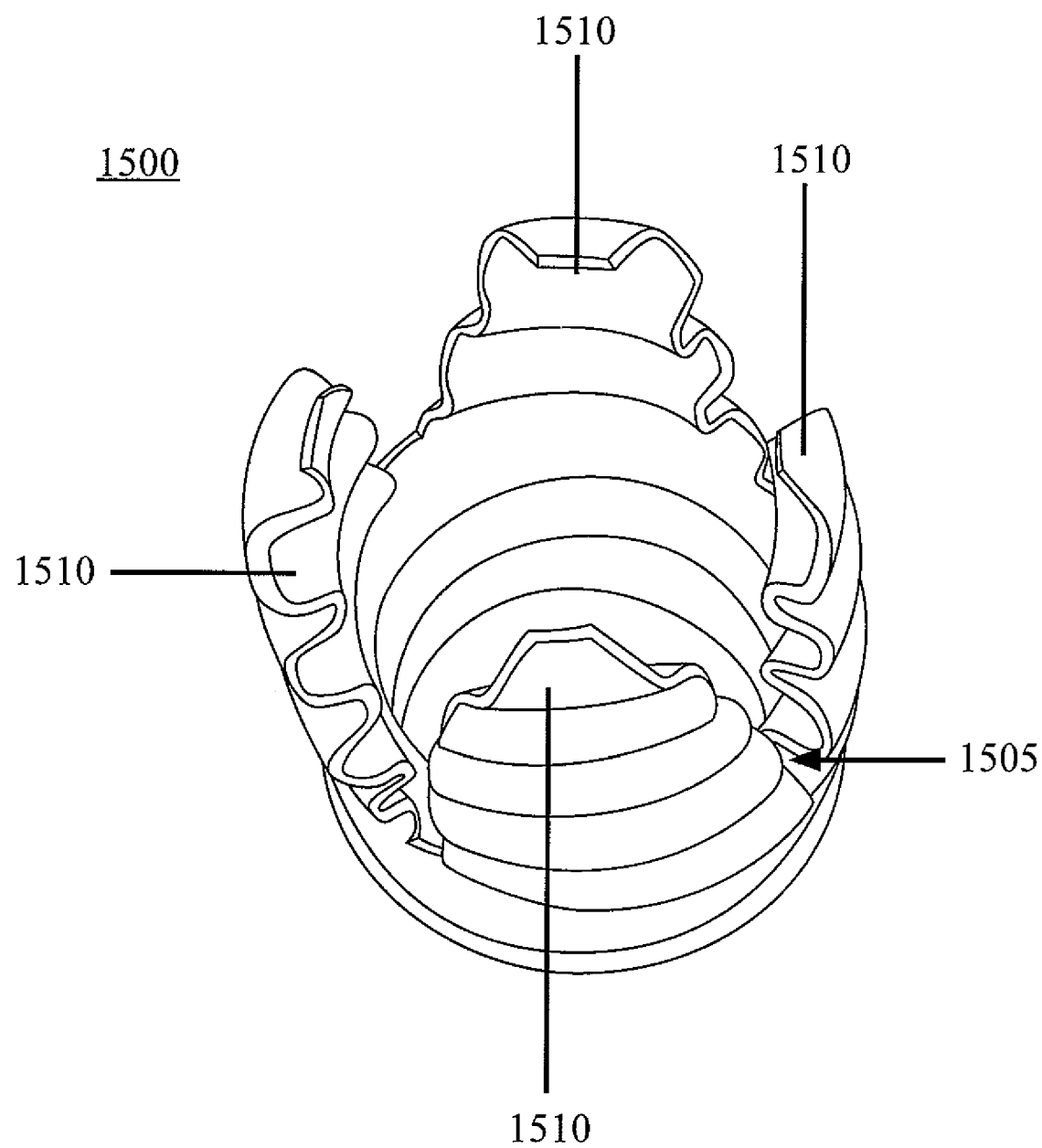
FIG. 15 is a perspective view of a guard having four flap-like elements according to one embodiment.

FIG. 15 illustrates another embodiment 1500 of a guard 1505 having four flap-like elements 1510.

In use, a male element with its cage type protector can have a smaller diameter than the diameter of a female protector, so that a male element can fit inside a female protector. A female guard may be sized to have a smaller diameter than a male guard, so a female guard and female element may fit within a male guard. A female protector need not be circular. Rather, it can be made of one or more "stacked" compressible rings, or can be helical.

For avoidance of doubt, the guards and protectors described herein are not limited in use to liquid-liquid connectors. Rather, any fluid-fluid connector can be designed and made based on the disclosure herein for use in any device, including respirators and other gas-gas connectors. Additionally, guards of this disclosure can be used to prevent unwanted contamination in the pharmaceutical and biotechnology industries, where sterility of connectors is desired.

To manufacture connectors with guards, one can obtain commercially available connectors and apply guards of this disclosure to them, thus producing a combined/guard product.

A person of ordinary skill in the art can use the disclosures and teachings contained herein to create variations without undue experimentation and with a reasonable likelihood of success. All such equivalents are considered part of this disclosure.

Embodiments of this disclosure have advantages over existing devices that do not have flexible protective structures. In DE 2843281; reference 7. Walterspiel, J N, Protective Ribs for Male Connectors. Inf. Control and Hospital Epidemiology 1988: 9(8): 342; and 8. Walterspiel, J N, Protective Ribs for Connectors, Inf. Control and Hospital Epidemiology 1986; 7(11): 564, the protectors were rigid. To use rigid protectors, it is necessary to standardize the number of rigid elements in the protector, and they complementary elements (male and female) must be very carefully connected. This can lead to increased difficulty, breakage of the protector elements, and loss of time, and increased likelihood of contamination. Additionally, use of rigid protectors generally require use of a rotating ring, so the male and female components can be screwed together without difficulty.

In contrast, with the use of the flexible, resilient protectors of this disclosure, it is easier to intercalate male and female components together and further reduce the likelihood of contamination of fluid in a luer or other connecting device.

Improved connectors of this disclosure can find wide use in medical, veterinary, research, biotechnology, chemical industries, and any other industry requiring sterile operations involving connecting fluid-carrying elements to each other.

Figure 16A:
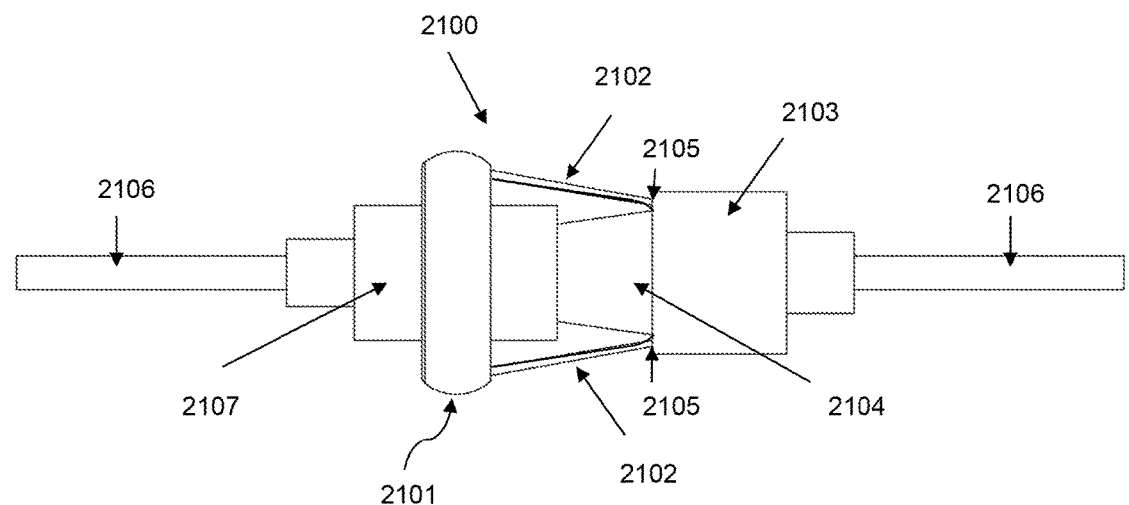
FIG. 16A is a side views of a connected intravenous line where the tip of a needleless valve connector is protected by a cowl that is attached to the base of a needleless valve connector, according to one embodiment.
Figure 16B:
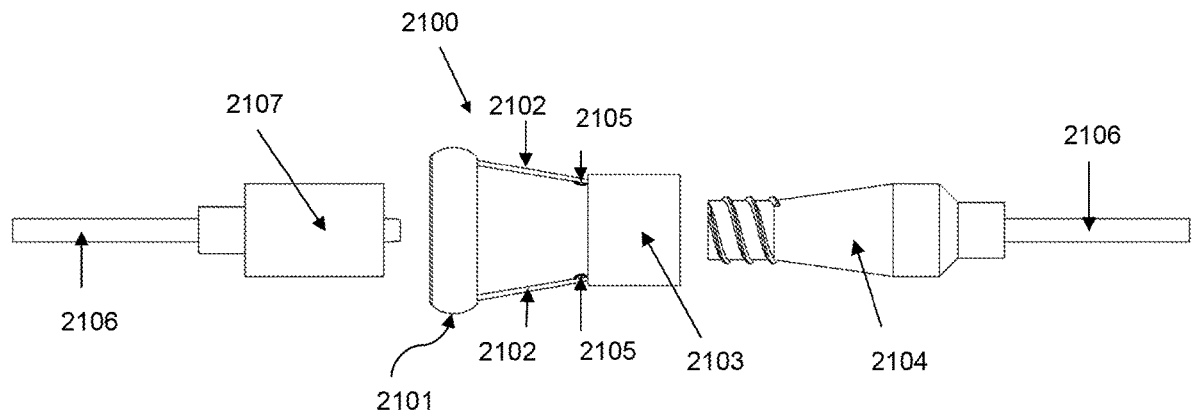
FIGS. 16B and 16C are side and perspective views, respectively, of the embodiment of FIG. 16A, where the parts are unconnected.
Figure 16:
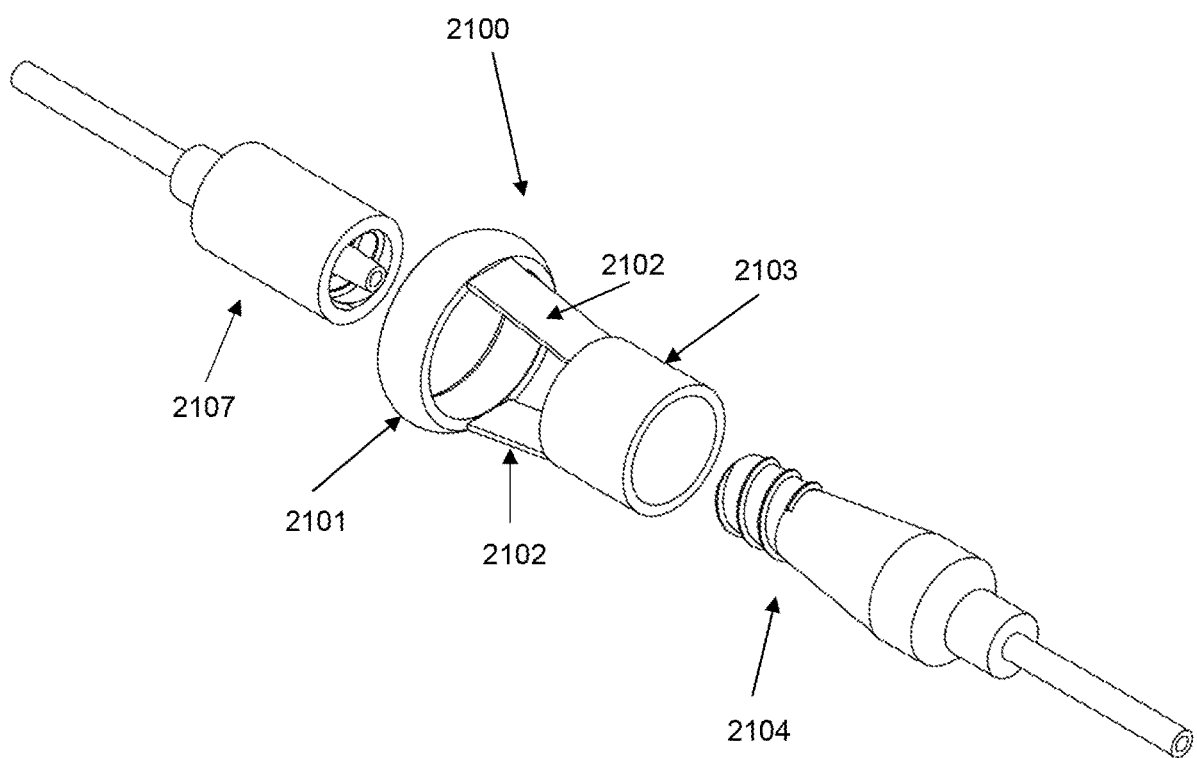

Referring now to FIGS. 16A-16C, another embodiment of a connector guard 2100 is illustrated in side/assembled view (FIG. 16A), side/disassembled view (FIG. 16B), and perspective/disassembled view (FIG. 16C). FIG. 16A shows the connector guard 2100 disposed over a connection of an intravenous line, which includes two tubes 2106, a male luer connector 2107, and a needleless valve connector 2104. The connector guard 2100 includes a ring 2101 (or "cowl"), with a convex or rounded outer surface to minimize the surface area of the ring 2101 that contacts other surfaces when it is laid down, etc. The ring 2101 is attached to two flat, flexible, outwardly bending, elastic couplers 2102, which are attached in turn to a cylindrical base 2103 (or "a second ring" or "clip"). When placed over the connection of the intravenous line, the ring 2101 resides over the male luer connector 2107, the base 2103 resides over the needless valve connector 2104, and the elastic couplers 2012 span between the ring 2101 and the base 2103. The elastic couplers 2102 may include reinforcements 2105 on the inside, to promote outward bending/flexing of the elastic couplers 2102 upon an axial compression of the shielding assembly. The ring 2101 can be axially (or "longitudinally") compressed towards the base 2103, thus causing the elastic couplers 2102 to bend or bow outward, for example when a health care worker sterilizes a connector tip, connects an intravenous line, or places an alcohol cap on a connector tip between infusions. The alcohol cap(s) and the sleeve of male luer connectors will fit through the ring 2101.

FIG. 16B is a disassembled side view of the connector guard 2100, the male luer connector 2107, and the needless valve connector 2104 of FIG. 16A. FIG. 16C is a disassembled perspective view. In some embodiments, the connector guard 2100 may be provided along with a connector.

Figure 17A:
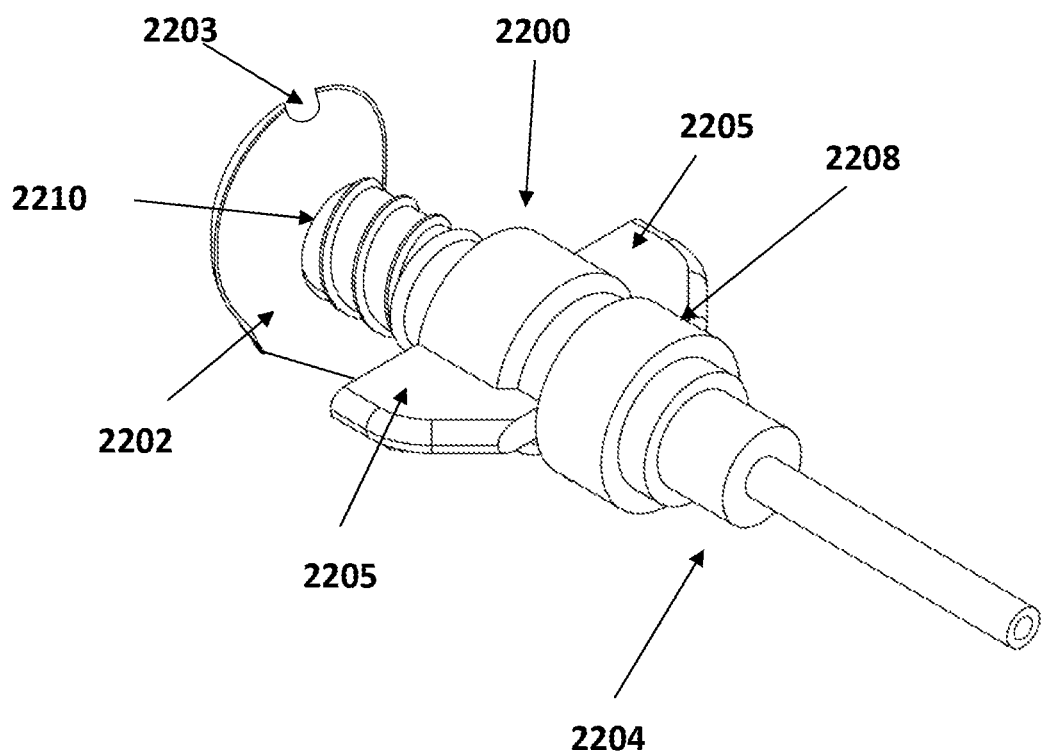
FIGS. 17A and 17B are perspective and side views, respectively, of a contact shield of an unconnected needleless female valve connector, according to one embodiment.
Figure 17B:
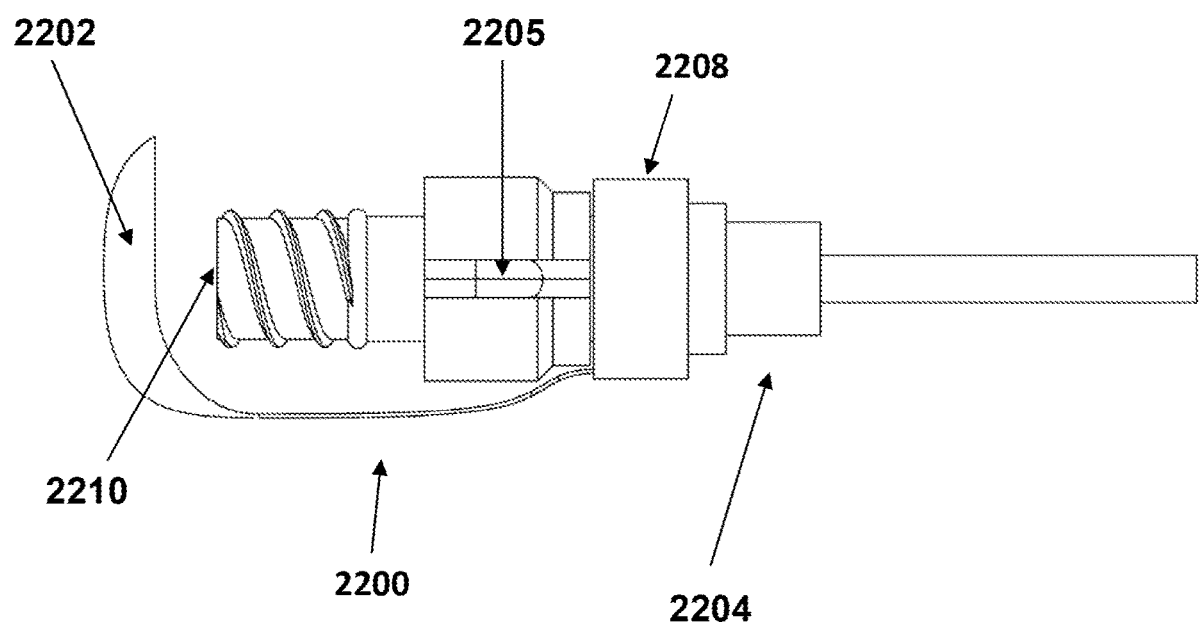

Referring now to FIGS. 17A and 17B, another embodiment of a connector guard 2200 is illustrated in perspective and side views, respectively. In this embodiment, the connector guard 2200 is attached to only one end of a medical tubing connector, which in this case is a needleless female valve connector 2204 having an exposed connection end 2210. The connector guard 2200 includes a base 2208, two wings 2205 attached to the base 2208 to facilitate manipulation and handling by a user, a curved shield 2202 extending laterally away from, and then curving forward away from, the base 2208, and a notch 2203 in the far edge of the shield 2202. In use, the connector guard 2200 is placed over the needleless female valve connector 2204 (or any other suitable tubing connector part), so that the shield 2202 curves out and around the open connection end 2210 of the needleless female valve connector 2204. The shield 2202 thus protects the connection end 2210 from contacting a user or any surface of another device or any other item.

As best seen in FIG. 17B, the shield 2202 has a shape that is similar to that of a cobra head. The base 2208 and wings 2205 may act like an ergonomic handle, to facilitate handling of the connector guard 2200 and help prevent repetitive motion damage to a healthcare worker's hands. The shield 2202 is rigid enough to protect the exposed connection end 2210, but it is also flexible enough to allow it to be bent/flexed out of the way by a healthcare worker who is cleaning the connection end 2210, connecting an intravenous line to the connection end 2210, placing an alcohol cap on the connection end 2210, or the like. Alcohol caps fit under the shield 2202, and the shield 2202 stays bent backwards when an infusion line is connected, where its rounded shape avoids it being caught on objects. To revert to and stay in the midline, relative to the connector 2204, the shield 2202 includes the notch 2203, to engage on the connected intravenous line that would be in front of it. Again, the connector guard 2200 may be used with any suitable type of protector, according to various embodiments.

Figure 18:
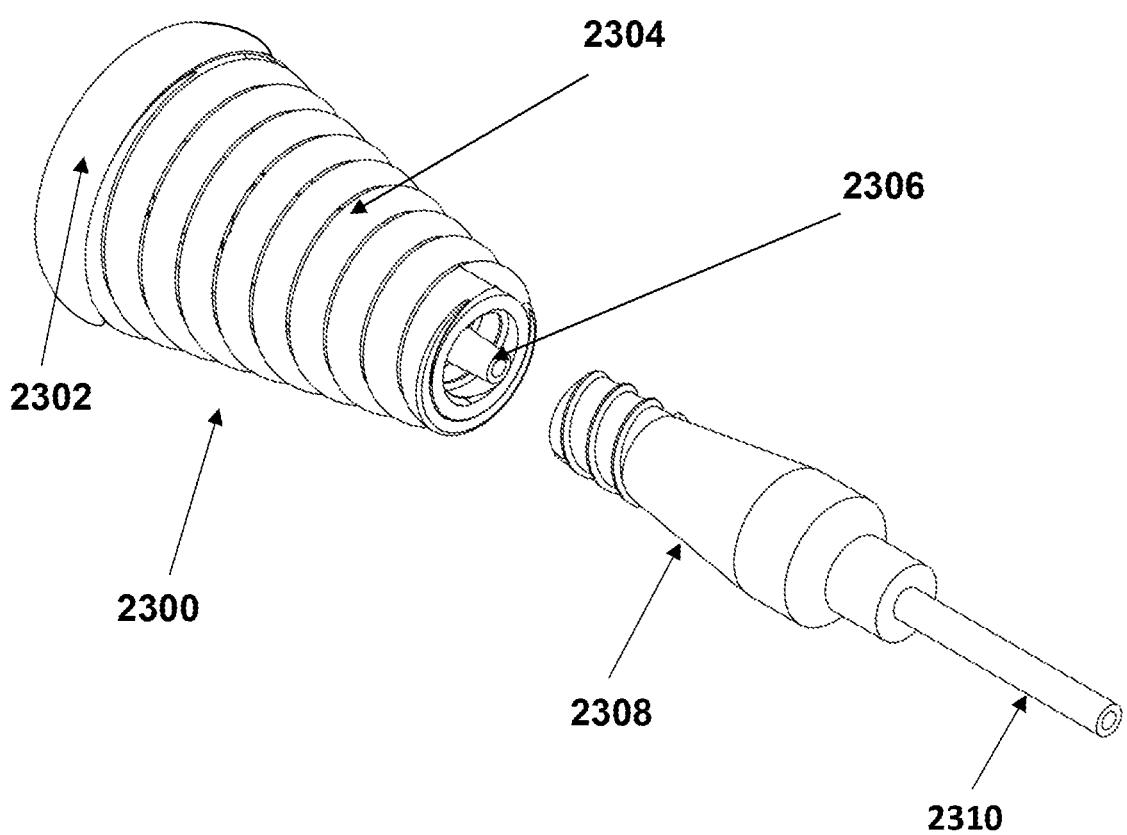
FIG. 18A is a perspective, unconnected view of a needless female valve connector whose tip is shielded by a rounded cowl that is connected to a funnel shaped compressible spring, according to one embodiment.
FIG. 18B is a side, cross-sectional, connected view of the embodiment of FIG. 18B.
Figure 18B:
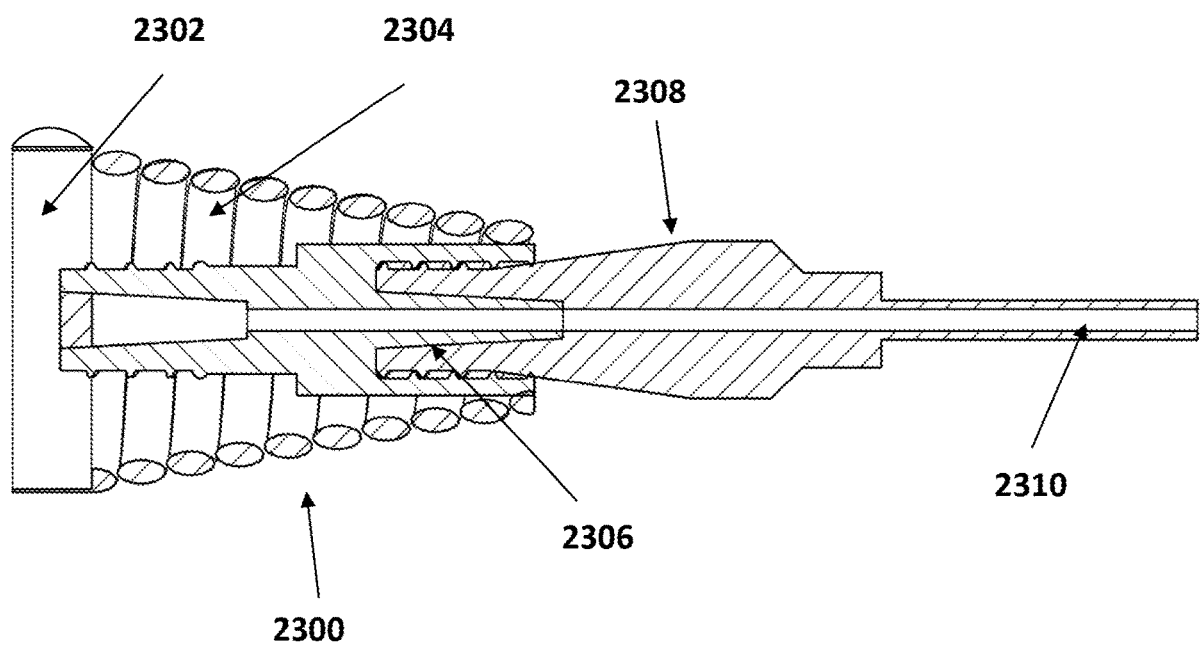

FIGS. 18A and 18B are perspective/unattached and side cross-sectional/attached views, respectively, of another embodiment of a connector guard 2300. These figures show a section of medical tubing 2310 with a female connector component 2308 on one end, and an a male connector component 2306 that connects with the female connector component 2308. The connector guard 2300 includes a ring 2302 (or "cowl") at its widest end, coupled with a spring portion 2304 (or "helix portion") ending in a final coil of the spring portion 2304 at the end opposite the ring 2302. The connector guard 2300 resides over the male connector component 2306 when the two connector components are separated, and it also protects at least part of the female connector component 2308 when the two components are connected (as in FIG. 16B). The ring 2302 and each of the coils of the spring portion 2304 has a convex, rounded outer surface and the coils, upon compression, slide over each other. The outer surfaces of the spring portion 2304 are rounded so that they slide more easily over surfaces with which they come in contact and to reduce the likelihood of coming into contact with contamination. The connector guard 2300 may be secured by current luer standard into another needleless valve connector and may be provided, as can the other embodiments disclosed herein, as a stand-alone device to be used/connected with any existing or as yet to be developed intravenous infusion equipment. Different sizes and shapes may be developed, using the characteristics of the connector guard 2300, to appropriately mate with different types and sizes of connectors.

Figure 19:
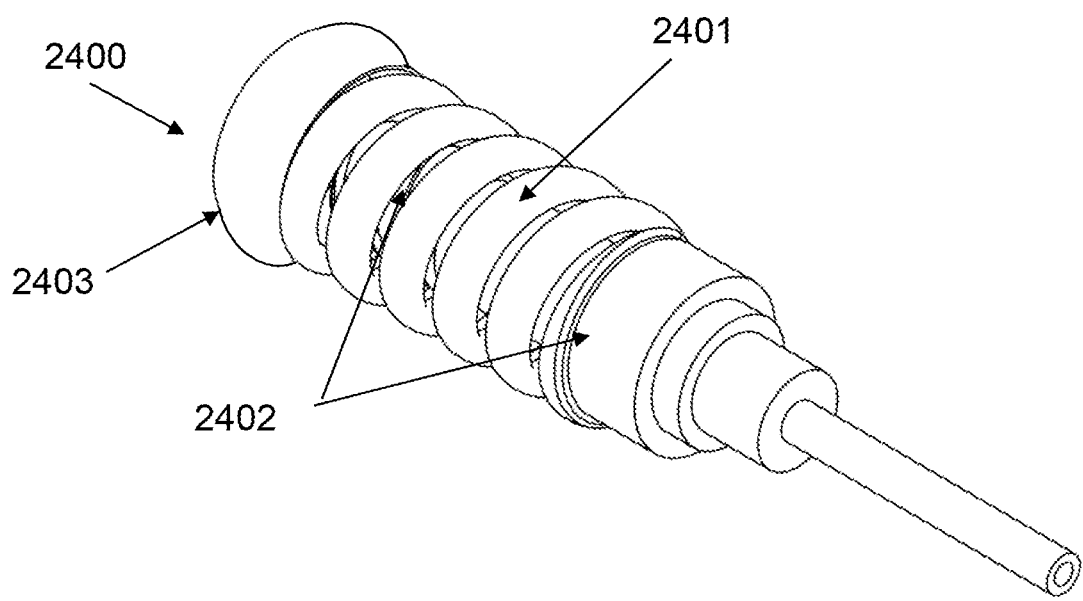
FIGS. 19A and 19B are perspective and cross-sectional views, respectively, of a needless female valve connector whose tip is shielded from contamination by a cowl connected to a compressible spring attached to the base of a needleless valve connector, according to one embodiment.
Figure 19:
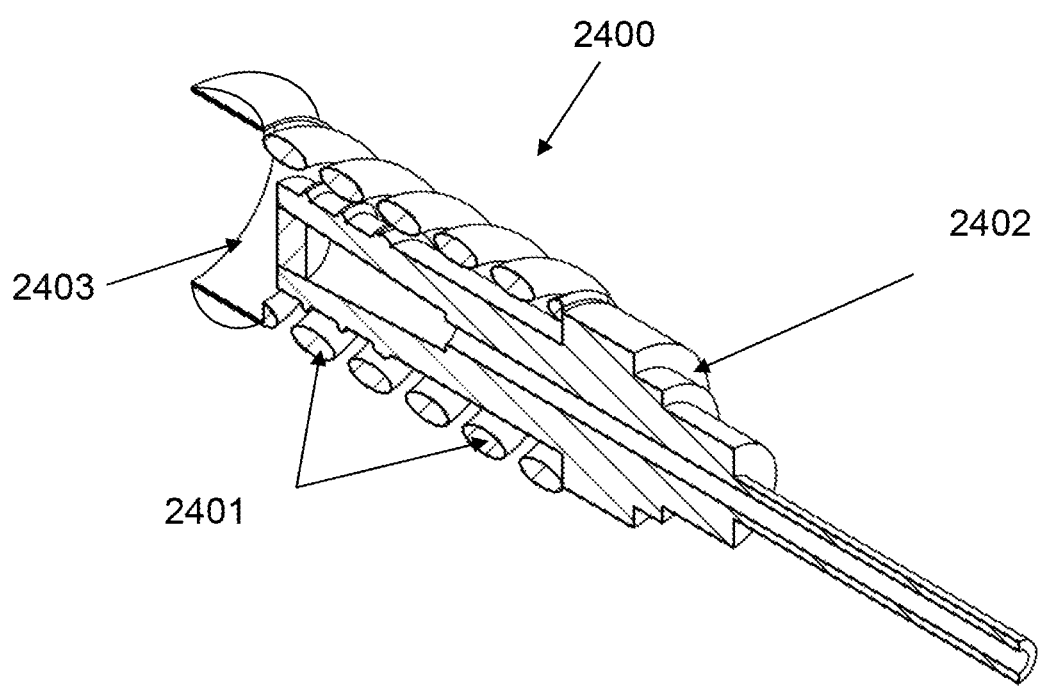

FIGS. 19A and 19B are perspective and cross-sectional views, respectively, of another embodiment of a connector guard 2400. This embodiment of the connector guard 2400 is similar to that shown in FIGS. 18A and 18B, in that it includes a ring 2403 at its widest end, coupled with a spring portion 2401, and ending in a final coil of the spring portion 2401. The guard 2400 is slightly different sized and shaped, however, and it is shown protecting a different type of connector 2402, thus illustrating that different configurations of connector guards 2400 may be provided for different types and sizes of connectors.

This is believed to be a complete and accurate description of embodiments and aspects of the invention. Alternative embodiments are contemplated within the scope of the invention, however, and the above description is intended for exemplary purposes and not to limit the scope of the invention as described, for example, in the following claims.

I claim:

1. A medical tubing connector assembly comprising:
   a first line;
   a second line;
   a first medical tubing connector coupled to the first line;
   a second medical tubing connector coupled to the second line;
   the first medical tubing connector including a first connection member selectively coupled with the second medical tubing connector; and
   a protective guard coupled to the first medical tubing connector, the protective guard comprising:
      a cylindrical base; and
      a curved shield having a rounded shape extending laterally away from the cylindrical base and beyond and around one end of the cylindrical base, the curved shield defining a notch in a far edge of the curved shield,
   wherein the cylindrical base fits over the first connection member of the first medical tubing connector,
   wherein the curved shield curves around an end of the first connection member,
   wherein the curved shield is spaced apart from the end of the first connection member,
   wherein, the protective guard protects the end of the first connection member from contamination,
   wherein the notch defines a curved indent that receives a portion of the second line when the second medical tubing connector is coupled to the first connection member of the first medical tubing connector,
   wherein the curved shield flexes outwardly away from the first medical tubing connector when the second medical tubing connector is coupled to the first connection member of the first medical tubing connector,
   wherein the notch engages and receives the portion of the second line into the curved indent, and
   wherein the curved shield is spaced sufficiently apart from the end of the first connection member such that an alcohol cap fits under the curved shield and onto the end of the first connection member.

2. The medical tubing connector assembly of claim 1, further comprising two wings extending from the cylindrical base to facilitate handling of the protective guard by a user.

3. The medical tubing connector assembly of claim 1, further comprising an orienting feature on the curved shield to indicate an orientation of the curved shield to a user.

4. The medical tubing connector assembly of claim 1, wherein the curved shield has a shape that is similar to that of a cobra head.

* * * * *